US007669995B2

(12) United States Patent
Ogle et al.

(10) Patent No.: US 7,669,995 B2
(45) Date of Patent: Mar. 2, 2010

(54) SEALING COMPONENT DEFINING FIRST, SECOND, AND THIRD SEALS

(75) Inventors: Holli C. Ogle, Corvallis, OR (US); John L. Taylor, Corvallis, OR (US); Marc A. Baldwin, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 12/421,103

(22) Filed: Apr. 9, 2009

(65) Prior Publication Data

US 2009/0191742 A1 Jul. 30, 2009

Related U.S. Application Data

(62) Division of application No. 11/115,586, filed on Apr. 27, 2005, now Pat. No. 7,533,976.

(51) Int. Cl.

*B41J 2/175* (2006.01)
*F16I 17/00* (2006.01)
*A61M 37/00* (2006.01)

(52) U.S. Cl. ........................... 347/86; 277/626; 604/86

(58) Field of Classification Search ................... 347/84, 347/85, 86, 87; 141/329; 215/247; 277/626, 277/627; 604/86, 87, 88, 90, 414
See application file for complete search history.

(56) References Cited

U.S. PATENT DOCUMENTS

| | | | | |
|---|---|---|---|---|
| 3,330,281 | A * | 7/1967 | Visser | 604/90 |
| 4,185,628 | A | 1/1980 | Kopfer | |
| 4,516,967 | A | 5/1985 | Kopfer | |
| 4,928,126 | A | 5/1990 | Asai | |
| 5,232,109 | A * | 8/1993 | Tirrell et al. | 215/247 |
| 5,544,858 | A | 8/1996 | Rogers et al. | |
| 5,790,158 | A | 8/1998 | Shinada et al. | |
| 5,949,458 | A | 9/1999 | Studholme | |
| 5,953,033 | A | 9/1999 | Salter et al. | |
| 6,332,674 | B1 | 12/2001 | Kamiyama et al. | |
| 6,682,184 | B2 | 1/2004 | Anderson et al. | |
| 6,692,118 | B2 | 2/2004 | Michele et al. | |
| 6,702,434 | B2 | 3/2004 | Barinaga et al. | |
| 6,739,709 | B2 | 5/2004 | Nip | |
| 2002/0084596 | A1 | 7/2002 | Michele et al. | |
| 2002/0093554 | A1 | 7/2002 | Smith et al. | |

(Continued)

FOREIGN PATENT DOCUMENTS

DE 19604819 8/1997

(Continued)

OTHER PUBLICATIONS

International Search Report for Application PCT/US2006/016288. Report issued on Oct. 2, 2006.

(Continued)

*Primary Examiner*—Anh T. N. Vo

(57) ABSTRACT

A sealing component includes an elastomeric material. An exterior side surface of the elastomeric material is to define at least a first seal with a first external mating member into which the sealing component is insertable. An interior surface of the elastomeric material is to define a second seal and a third seal with a second external mating member insertable into the sealing component.

12 Claims, 12 Drawing Sheets

U.S. PATENT DOCUMENTS

| | | | |
|---|---|---|---|
| 2003/0189624 | A1 | 10/2003 | Rehman et al. |
| 2004/0233260 | A1 | 11/2004 | Shinada et al. |
| 2004/0257412 | A1 | 12/2004 | Anderson, Jr. et al. |
| 2005/0043689 | A1 | 2/2005 | Chen |

FOREIGN PATENT DOCUMENTS

| | | |
|---|---|---|
| EP | 1090767 | 4/2001 |

OTHER PUBLICATIONS

English translation of First Office Action issued by State Intellectual Property Office, Peoples Republic of China on May 8, 2009 for patent application No. 200680013988.9, application filing Apr. 26, 2006.

* cited by examiner

SEALING COMPONENT DEFINING FIRST, SECOND, AND THIRD SEALS

CROSS-REFERENCE TO RELATED APPLICATIONS

This application is a Divisional of U.S. patent application Ser. No. 11/115,586, filed on Apr. 27, 2005, now U.S. Pat. No. 7,533,976 which is incorporated herein by reference.

BACKGROUND

Inkjet-printing devices, such as inkjet printers, operate by ejecting ink onto media to form images on the media. For instance, a printhead may be moved back and forth across the media, and the media advanced perpendicular to the movement of the printhead across the media. While the inkjet printhead moves across the media, it ejects ink onto the media to form an image.

At least in some types of inkjet-printing devices, traditionally the inkjet printhead and the ink have been encased in an enclosure known as an inkjet cartridge. Usually the ink of the cartridge is depleted before the inkjet printhead requires replacement. Thus, when the ink runs out, a new cartridge has to be inserted into the printer. More recently, the inkjet printhead has been separated from the ink supply as separately replaceable consumable items. An inkjet printhead may be inserted into an inkjet-printing device, and then just a supply of ink may be mated with the printhead already installed within the printing device, or before the printhead is installed.

Where the ink is encased in a supply separate from the inkjet printhead, the mating process between the printhead and the supply should ensure that there are no resulting fluid leaks. Furthermore, a supply may be later removed from the printhead before the ink therein is depleted. When the supply is so removed, as well as before the supply is first mated with the printhead, there should also be no fluid leaks.

BRIEF DESCRIPTION OF THE DRAWINGS

The drawings referenced herein form a part of the specification. Features shown in the drawing are meant as illustrative of only some embodiments of the invention, and not of all embodiments of the invention, unless otherwise explicitly indicated.

DETAILED DESCRIPTION OF THE DRAWINGS

Figure 1A:
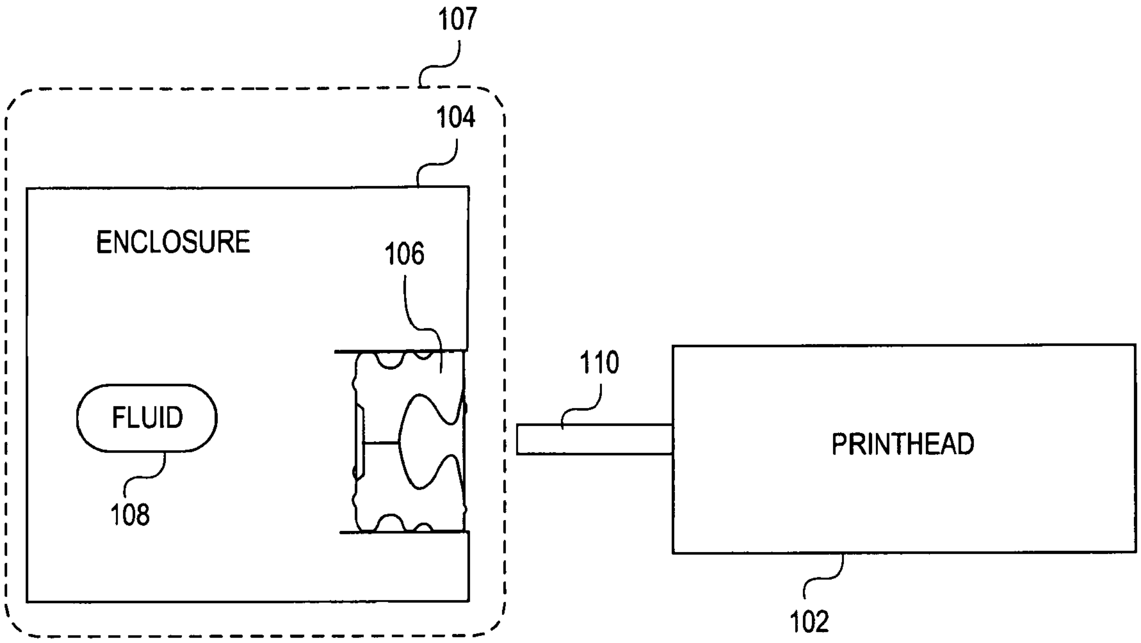
FIGS. 1A, 1B, 1C, and 1D are diagrams showing a sealing component inserted into a rudimentary enclosure of fluid, and a rudimentary printhead being inserted into and removed from the enclosure through the sealing component, according to an exemplary embodiment of the invention.

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

FIGS. 1A, 1B, 1C, and 1D show a printhead 102 being inserted into and removed from an enclosure 104 of fluid 108 through a sealing component 106, according to an exemplary embodiment of the invention. The printhead 102 has a needle 110 or another mating member that is able to pierce the sealing component 106 to access the fluid 108 encased within the enclosure 104. The printhead 102 is more generally an external mating member, in that it is a member that mates with the sealing component 106, and that is external to the sealing component 106. The printhead 102 may be part of an inkjet-printing device, such as an inkjet printer, where may be instances of the enclosure 104 for each different color of ink used in the device for forming images on media.

The fluid 108 encased within the enclosure 104 may be ink in one embodiment. The enclosure 104 may be considered an ink supply, or a part of an ink supply, in one embodiment. For instance, the dotted line 107 surrounding the enclosure 104 and the sealing component 106 in FIG. 1A in particular is indicative of an ink supply in one embodiment, which may include the enclosure 104, the sealing component 106, and potentially the fluid 108.

The enclosure 104 is also generally a mating member, in that it is a member that mates with the sealing component 106. When considering the sealing component 106 alone, the enclosure 104 is an external mating member, since the enclosure 104 is external to the sealing component 106. When considering the sealing component 106 in conjunction with the enclosure 104, such as two parts of an ink supply, the enclosure 104 is an internal mating member, since the enclosure 104 is a part of the same supply of which the sealing component 106 is a part.

In general, the sealing component 106 seals with the enclosure 104 so that the fluid 108 cannot leak or escape therefrom. The sealing component 106 is specifically inserted into a hole or other opening of the enclosure 104. In FIG. 1A, the needle 110 of the printhead 102 has not yet been inserted into the enclosure 104 through the sealing component 106. As such, the sealing component 106 seals with the enclosure 104 in FIG. 1A, and the sealing component 106 can seal with itself to ensure that the fluid 108 cannot leak or escape therefrom. It is noted that the needle 110 has an inner channel extending across its length so that when the needle 110 is inserted into the enclosure 104, it is able to access the fluid 108 encased therein. As such, the needle 110 may be considered to be a hollow needle, and is more generally a mating member.

Figure 1B:
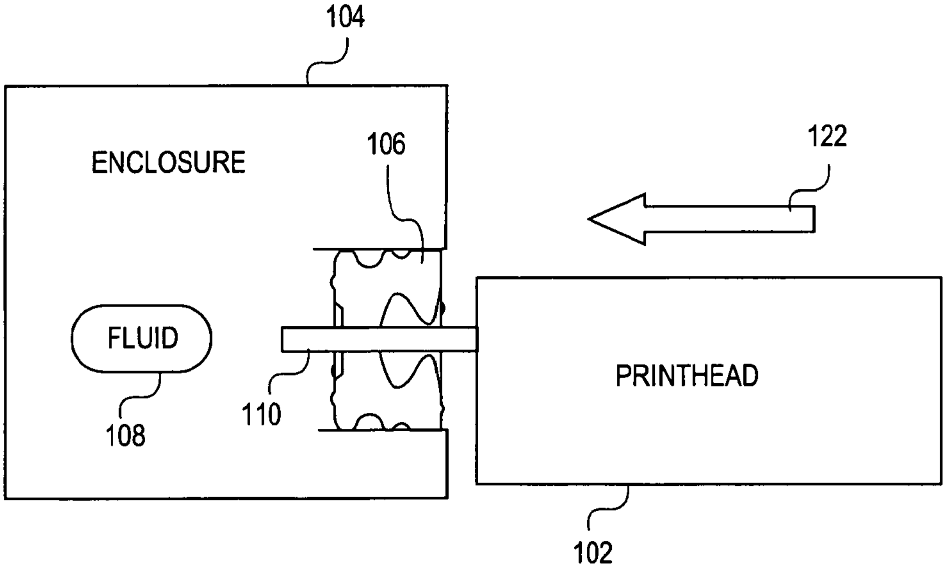

In FIG. 1B, the needle 110 of the printhead 102 is in the process of being inserted into the enclosure 104 through the sealing component 106, as indicated by the arrow 122. As the needle 110 is inserted through the sealing component 106, the sealing component 106 seals with the needle 110 so that the fluid 108 cannot leak or escape. Thus, in FIG. 1B, there are two acts of sealing being performed by the sealing component 106: the sealing component 106 sealing with the enclosure 104, and the sealing component 106 sealing with the needle 110 of the printhead 102.

Figure 1C:
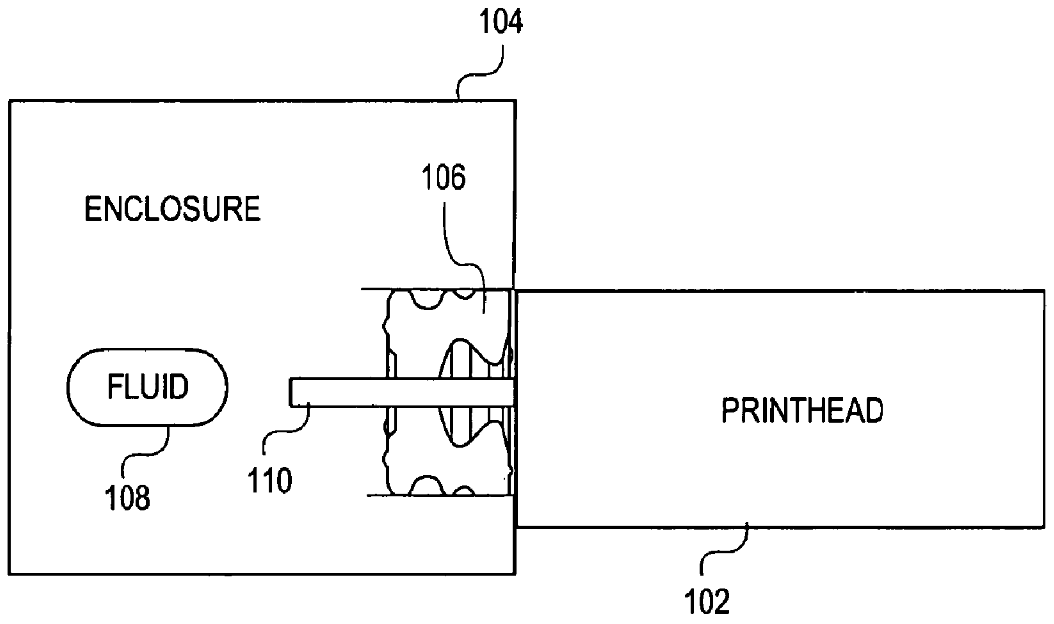

In FIG. 1C, the needle 110 of the printhead 102 has been completely inserted into the enclosure 104 through the sealing component 106. As such, the printhead 102 is now able to access the fluid 108 encased within the enclosure 104, through the needle 110 thereof. The sealing component 106 again seals with both the needle 110 and the enclosure 104 so that the fluid 108 cannot leak or escape.

Figure 1D:
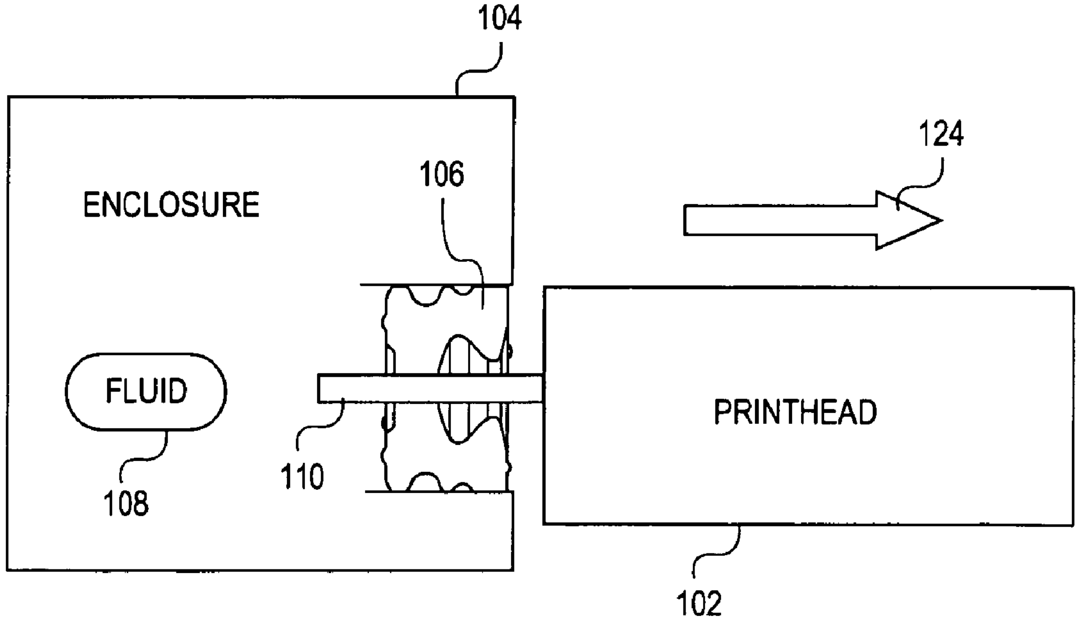

In FIG. 1D, the needle 110 of the printhead 102 is in the process of being removed from the enclosure 104 through the sealing component 106, as indicated by the arrow 124. As the needle 110 is removed through the sealing component 106, the sealing component 106 still seals with the needle 110 so that the fluid 108 cannot leak or escape. Thus, in FIG. 1D, there are still two acts of sealing being performed by the sealing component 106: the sealing component 106 sealing with the enclosure 104, and the sealing component 106 sealing with the needle 110. After performance of the process depicted in FIG. 1D, and the needle 110 is completely removed from the enclosure 104, the enclosure 104 is again in the state depicted in FIG. 1A. Thus, the sealing component 106 can again seal with itself, such that the enclosure 104 prevents the escape of the fluid 108.

Figure 2A:
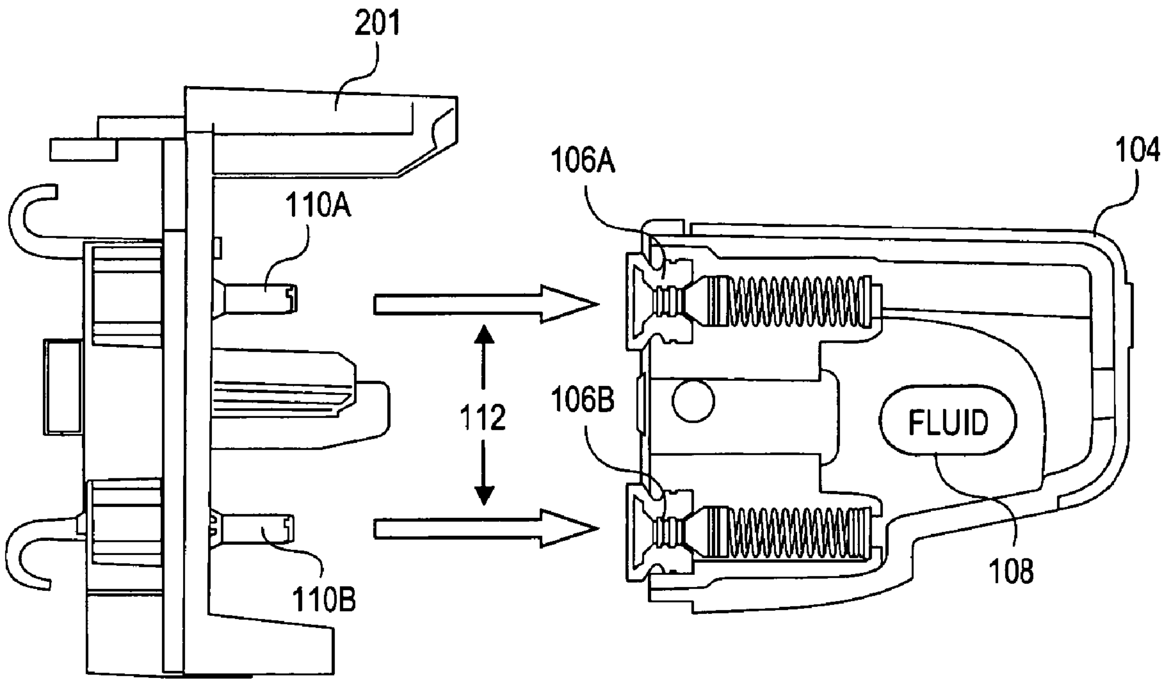
FIGS. 2A and 2B are diagrams depicting insertion of a printhead adapter into an enclosure of fluid through a sealing component, according to a more specific exemplary embodiment of the invention.
Figure 2B:
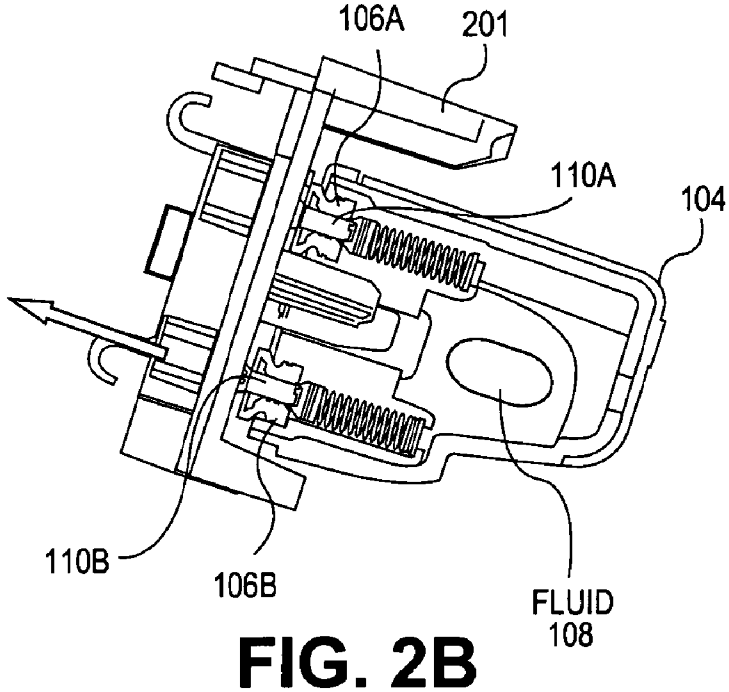

FIGS. 2A and 2B show a more specific implementation of an exemplary printhead adapter 201 being mated with a more specific implementation of the enclosure 104 of fluid 108 via sealing components 106A and 106B, according to an embodiment of the invention. The printhead adapter 201 ultimately mates with or is coupled to the printhead 102, such as via assorted tubes and/or housings. There are two needles 110A and 110B, corresponding to the two sealing components 106A and 106B. As before, the fluid 108 encased within the enclosure 104 may be ink, and the enclosure 104 may be an ink supply or a part of an ink supply.

In FIG. 2A, the printhead adapter 201 is in the process of being mated with the enclosure 104 via the needles 110A and 110B being inserted into the enclosure 104 through the sealing components 106A and 106B, as indicated by the arrows 112. In FIG. 2B, the printhead adapter 201 has been mated with the enclosure 104, via the needles 110A and 110B having been inserted into the enclosure 104 through the sealing components 106A and 106B.

In the embodiment of FIGS. 2A and 2B, the top needle 110A may allow air to be released into the enclosure 104 as the bottom needle 110B draws the fluid 108 from the enclosure 104. Having two sealing components 106A and 106B ensures that both needles 11A and 110B are sealed. Allowing air to be released into the enclosure 104 as the fluid 108 is drawn from the enclosure 104 ensures that internal pressure within the enclosure 104 remains at least substantially constant as the fluid 108 is depleted from the enclosure 104.

Figure 2C:
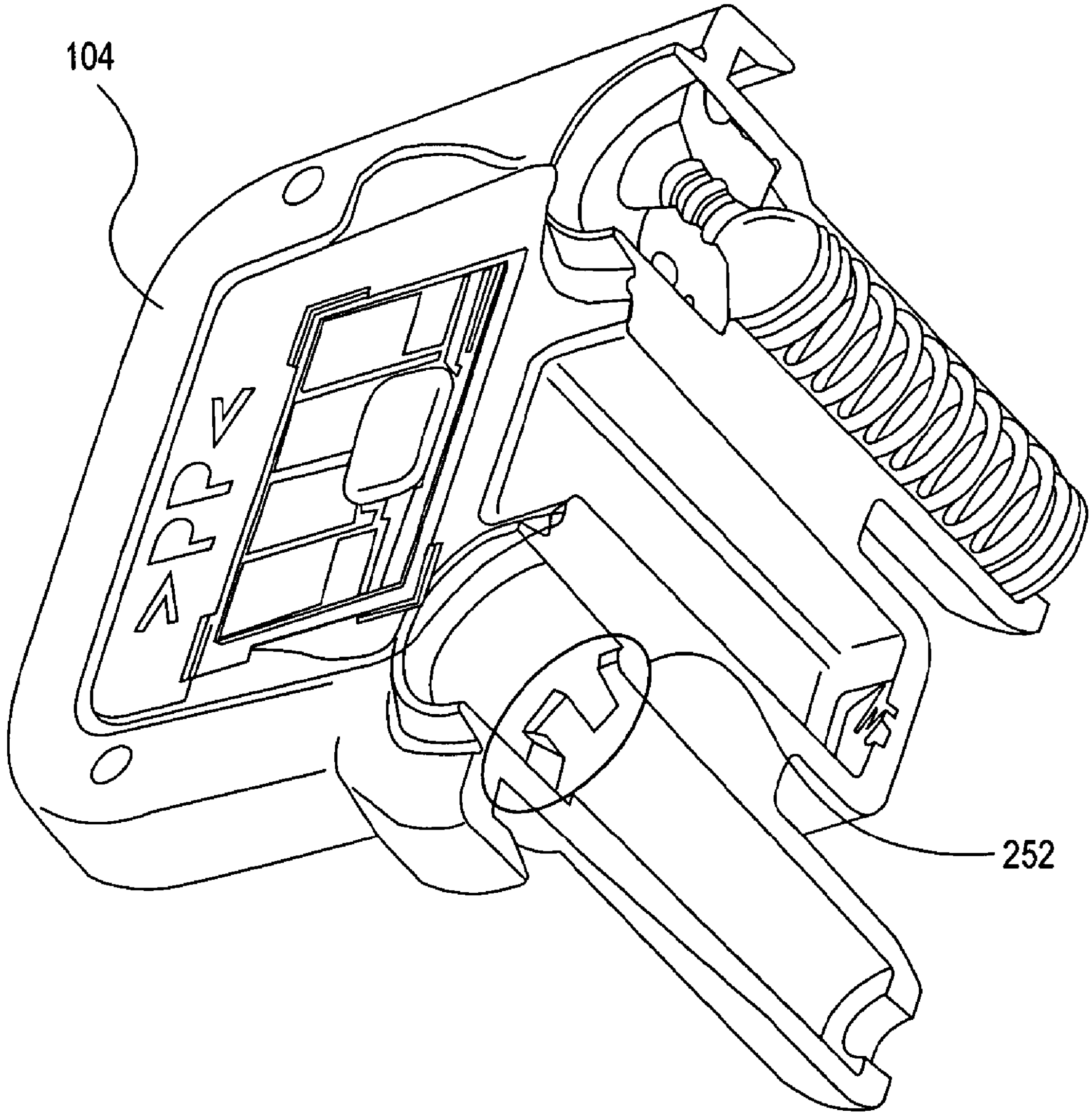
FIG. 2C is a diagram of a supply or enclosure into which a sealing component can be inserted, according to the same specific exemplary embodiment of the invention of FIGS. 2A and 2B.

FIG. 2C shows in detail a portion of the enclosure 104, according to a specific embodiment of the invention. As before, the enclosure 104 is intended to encase fluid, such as the fluid 108 of FIGS. 1A, 1B, 1C, 1D, 2A, and 2B, and may be or may be part of an ink supply. FIG. 2C depicts the enclosure 104 as having features, shown here as castellations 252, within an interior portion of the enclosure 104 wherein the sealing component 106 is to be inserted. In this example, castellations 252 are tabs, or a tabbed formation of grooves or notches, extending around the interior portion of the enclosure 104 within which the sealing component 106 is to be inserted.

The castellations 252 ensure that the sealing component 106 can be inserted into the enclosure 104 in a more secure manner than if the castellations 252 were not otherwise present. In particular, when the sealing component 106 is inserted into the enclosure 104, air can be trapped such that the sealing component 106 may not be able to be completely seated. For instance, there may be a solid shelf extending around the interior portion of the enclosure 104 within which the sealing component 106 is to be inserted, and against which the sealing component 106 is to be pressed. Inserting the sealing component 106 into the sealing component 106 may trap air such that the air has nowhere to go except against the solid shelf, resulting in the sealing component 106 not being completely seated.

By comparison, the presence of the castellations 252 allows such air to be lodged on the notches or grooves thereof, so that the sealing component 106 is able to be more completely seated. That is, any air that is trapped during insertion of the sealing component 106 can be lodged within the notches or grooves of the castellations 252. As such, the sealing component 106 may be able to be pushed inward within the enclosure 104 as far as it is supposed to go, and thus be completely seated within the enclosure 104.

Figure 3A:
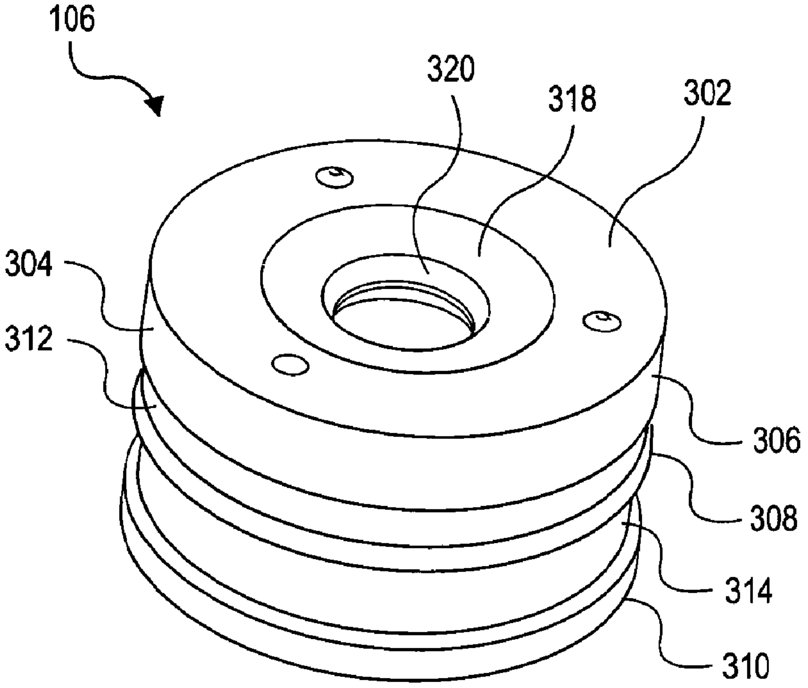
FIGS. 3A, 3B, 3C, and 3D are diagrams of a sealing component, according to one exemplary embodiment of the invention.
Figure 3B:
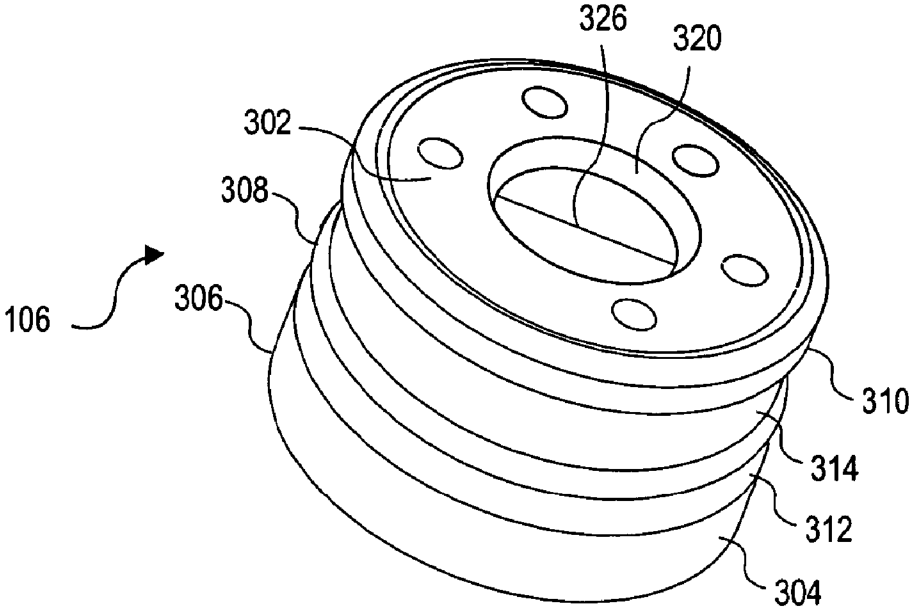
Figure 3C:
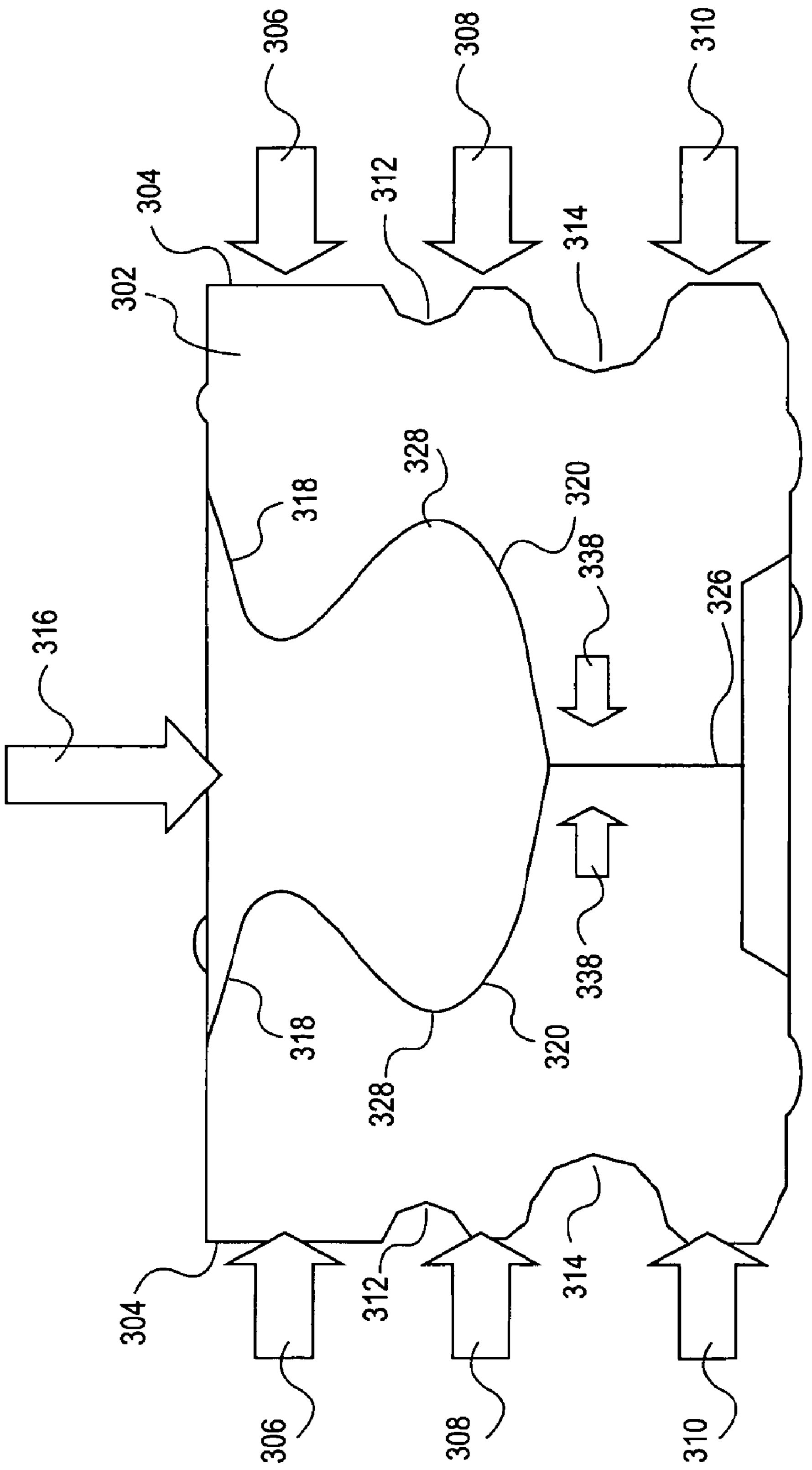
Figure 3D:
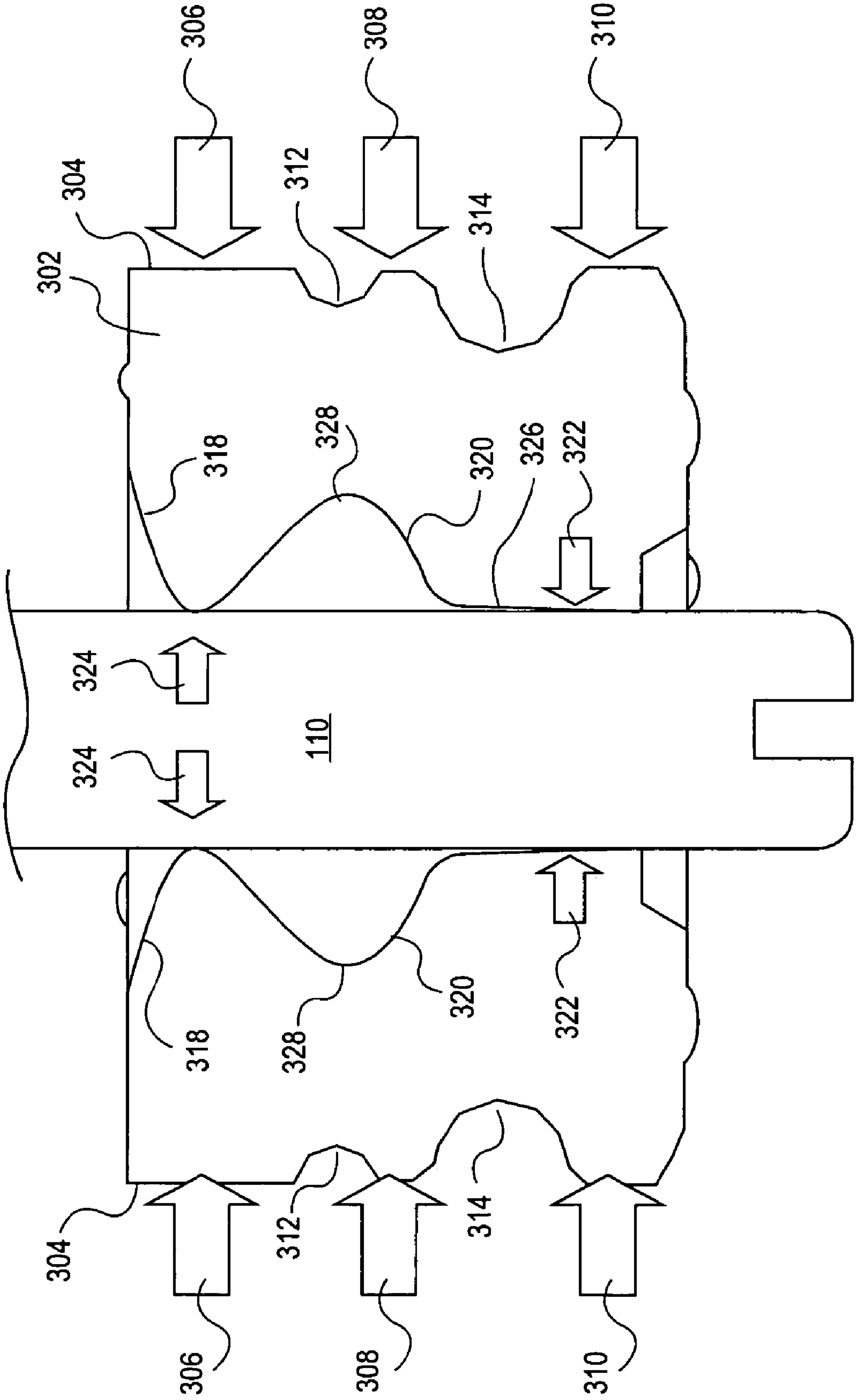

FIGS. 3A, 3B, 3C, and 3D show a specific implementation of the sealing component 106, according to an exemplary embodiment of the invention. FIG. 3A shows a top perspective view of the sealing component 106, whereas FIG. 3B shows a bottom perspective view of the sealing component 106. FIG. 3C shows a cross-sectional side view of the sealing component 106, where the needle 110 has not been inserted into the sealing component 106. FIG. 3D shows a cross-sectional side view of the sealing component 106, where the needle 110 has been inserted into the sealing component 106. The sealing component 106 may be fabricated from an elastomeric material 302, such as rubber or another elastomeric material. In describing the sealing component 106 of FIGS. 3A, 3B, 3C, and 3D, primary reference is made to the cross-sectional side views of FIGS. 3C and 3D, with supplemental reference as needed to the perspective views of FIGS. 3A and 3B.

The sealing component 106 has an exterior side surface 304. Upon insertion of the sealing component 106 into an external or internal mating member, such as the hole or opening of the enclosure 104 as depicted in FIGS. 1A, 1B, 1C, and 1D, the exterior side surface 304 defines at least one seal with this mating member. That is, the mating member mates with the sealing component 106 to define at least one of the seals indicated by the reference numbers or arrows 306, 308, and 310. Where the hole or opening of the mating member and the sealing component 106 are both round in shape, these seals may be considered annular seals.

The seals indicated by the reference numbers or arrows 306 and 308 are the primary seals defined by the exterior side surface 304 with the mating member into which the sealing component 106 is inserted. That is, the exterior side surface 304 of the sealing component 106 is designed so that the seals indicated by the reference numbers or arrows 306 and 308 are defined when the sealing component 106 is inserted into the mating member. By comparison, the seal indicated by the reference number or arrow 310 may or may not be defined, in that the exterior side surface 304 is not necessarily designed so that this seal is defined when the sealing component 106 is inserted into the mating member, as is described in more detail in the next two paragraphs.

When the sealing component 106 is inserted into the mating member, the seals indicated by the reference numbers or arrows 306 and 308 are defined because the elastomeric material 302 at these portions of the exterior side surface 304 are pushed or compressed into a compression region 312. The compression region 312 is a groove notched or otherwise fabricated within, and defined by, the exterior side surface 304 so that the elastomeric material 302 can so compress into the region 312 when these seals are being defined. By comparison, the region 314 may be a compression region defined by the exterior side surface 304 into which the elastomeric material 302 is pushed or compressed into where the seal identified by the reference number 310 is defined.

However, the region 314, and the area identified by the reference number or arrow 310, more generally constitute a manufacturing tolerance region, the dimensions of which do not affect definition of the seals identified by the reference numbers or arrows 306 and 308. As such, the dimensions of the manufacturing tolerance region can be varied during manufacture or fabrication of the sealing component 106, without affecting the functionality of the seals identified by the reference numbers or arrows 306 and 308. In this way, the seal identified by the reference number or arrows 310 may or may not be defined, depending on the manufacture of the sealing component 106.

Furthermore, the exterior side surface 304 of the sealing component 106 is asymmetrically shaped, so that a user is able to easily determine the proper orientation of the sealing component 106 when it is inserted into the mating member. The sealing component 106 of FIGS. 3A, 3B, 3C, and 3D is to be inserted into the mating member with a specific orientation, such that the portion of the sealing component 106 indicated by the arrows 310 is first inserted into the mating member, and the portion of the sealing component 106 indicated by the arrows 306 is inserted last into the mating member. The region 314 may thus be considered an orientation region defined by the exterior side surface 304 to render the shape of the exterior side surface 304 asymmetric, so that the user is able to easily discern the proper orientation of the sealing component 106.

Another mating member, such as an external mating member like the needle 110 of the printhead 102 of FIGS. 1A, 1B, 1C, and 1D, is insertable into the sealing component 106, as indicated by the arrow 316 in FIG. 3C (as well as the arrow 122 in FIG. 1B), and as specifically depicted in FIG. 3D. The sealing component 106 has an interior surface 320. When such a mating member is inserted into the sealing component 106, the interior surface 320 defines at least two seals with the mating member, one seal indicated by the arrows 322 in FIG. 3D, and another seal indicated by the arrows 324 in FIG. 3D. It is noted that the seals indicated by the arrows 322 and 324 are not present unless the mating member has been inserted into the sealing component 106.

When the mating member is first inserted into the sealing component 106, a lead-in region 318 of the sealing component 106 guides the mating member into the sealing component 106. The lead-in region 318 is thus a downward-ramped region defined by the interior surface 320, which if contacted by the mating member as it is inserted into the sealing component 106, results in the mating member being guided further inward into the sealing component 106. As the mating member further is inserted into the sealing component 106, the interior surface 320 defines a seal with the mating member, as indicated by the arrows 324 in FIG. 3D. This seal may be considered an annular seal where the interior surface 320 and the mating member each have a round shape. To assist the mating member into and past the regions of the interior surface 320 indicated by the arrows 324 and 322 in FIG. 3D, and by the arrows 338 in FIG. 3C, lubricating fluid, lubricating grease, or another type of lubricant may be used in one embodiment.

As the mating member is further inserted into the sealing component 106, it encounters a slit 326. Generally the slit 326 is a piercing of the sealing component 106 thereat, such as resulting from inserting a round needle into the sealing component 106 to result in the slit 326. The slit 326 may thus in one embodiment be round or partially round in shape. It is noted that a slight gap is depicted between the needle 110 and the sealing component 106 in FIG. 3D so that the slit 326 can be more clearly depicted in FIG. 3D. However, in actuality, this gap may not be present.

Prior to the mating member reaching the slit 326, the interior surface 320 of the sealing component 106 defines a seal with itself as indicated by the arrows 338 in FIG. 3C. That is, elastomeric material 302 of the sealing component 106 exerts sufficient force at both sides of the slit 326 to define the seal indicated by the arrows 338 in FIG. 3C. This seal prevents fluid at the bottom side of the sealing component 106 from escaping or leaking.

Once the mating member encounters the slit 326, it pushes through and past the slit 326 to reach the fluid at the other side of the sealing component 106, to access this fluid. The interior surface 320 of the sealing component 106 defines another seal, indicated by the arrows 322 in FIG. 3D, with the mating member once the mating member has been pushed through the slit 326. Thus, there are two seals defined between the interior surface 320 of the sealing component 106 and the mating member: the seal identified by the arrows 324 in FIG. 3D, and the seal identified by the arrows 322 in FIG. 3D.

Having two seals defined between the interior surface 320 of the sealing component 106 and the mating member inserted into the sealing component 106 provides for redundancy. If one of the seals should fail, the other seal is still present to prevent fluid leakage or escape. Furthermore, the seals indicated by the arrows 322 and 324 are defined because the elastomeric material 302 at these portions of the interior surface 320 are pushed or compressed into a compression region 328. The compression region 328 is a groove or notch removed from or otherwise fabricated within, and defined by, the interior surface 320 so that the elastomeric material 302 can compress into the region 328 when these seals are being defined.

Once the mating member has been inserted into the sealing component 106, it may be removed by being pulled from the sealing component 106. As the mating member is pulled from the sealing component 106, the seal identified by the arrows 322 is first broken. However, at the same time the seal formed by the interior surface 320 with itself, identified by the arrows 338 in FIG. 3C, is defined, so that the fluid to the other side of the sealing component 106 does not leak or escape. This seal formed by the interior surface 320 with itself, at the slit 326, is formed at any time when the needle 110 is not inserted at least partially into the slit 326. Thus, after the needle 110 has been removed from the sealing component 106 past the slit 326, the seal identified by the arrows 338 is formed. Similarly, while the needle 110 is being inserted into the sealing component 106, but before it has reached the slit 326, the seal identified by the arrows 338 is formed. Likewise, when the needle 110 is not inserted at all within the sealing component 106, this seal is formed.

The protrusion of the elastomeric material 302 at the interior surface 320 indicated by the arrows 324 serve further functionality in addition to defining a seal, when the mating member is being removed from the sealing component 106. As the mating member is being pulled from the sealing component 106, any fluid, such as ink, remaining on the sides of the mating member is at least substantially wiped off, or cleaned, by this protrusion. That is, the arrows 324 denote a wiping region defined by the interior surface 320 to at least partially clean the mating member as it is being removed from the sealing component 106.

Finally, once the mating member has been sufficiently removed from the sealing component 106 such that it clears the protrusion identified by the arrows 324, the seal defined by the interior surface 320 with the mating member, and denoted by the arrows 324, is broken. Thus, first the seal defined by the interior surface 320 with the mating member denoted by the arrows 322 is broken, and next the seal defined by the interior surface 320 with the mating member denoted by the arrows 324 is broken, as the mating member is removed from the sealing component 106. The order of these seals is reversed when the seals are being defined upon insertion of the sealing component 106, where first the seal identified by the arrows 324 is defined by the interior surface 320 with the mating member, and next the seal identified by the arrows 322 is defined by the interior surface 320 with the mating member.

Figure 4:
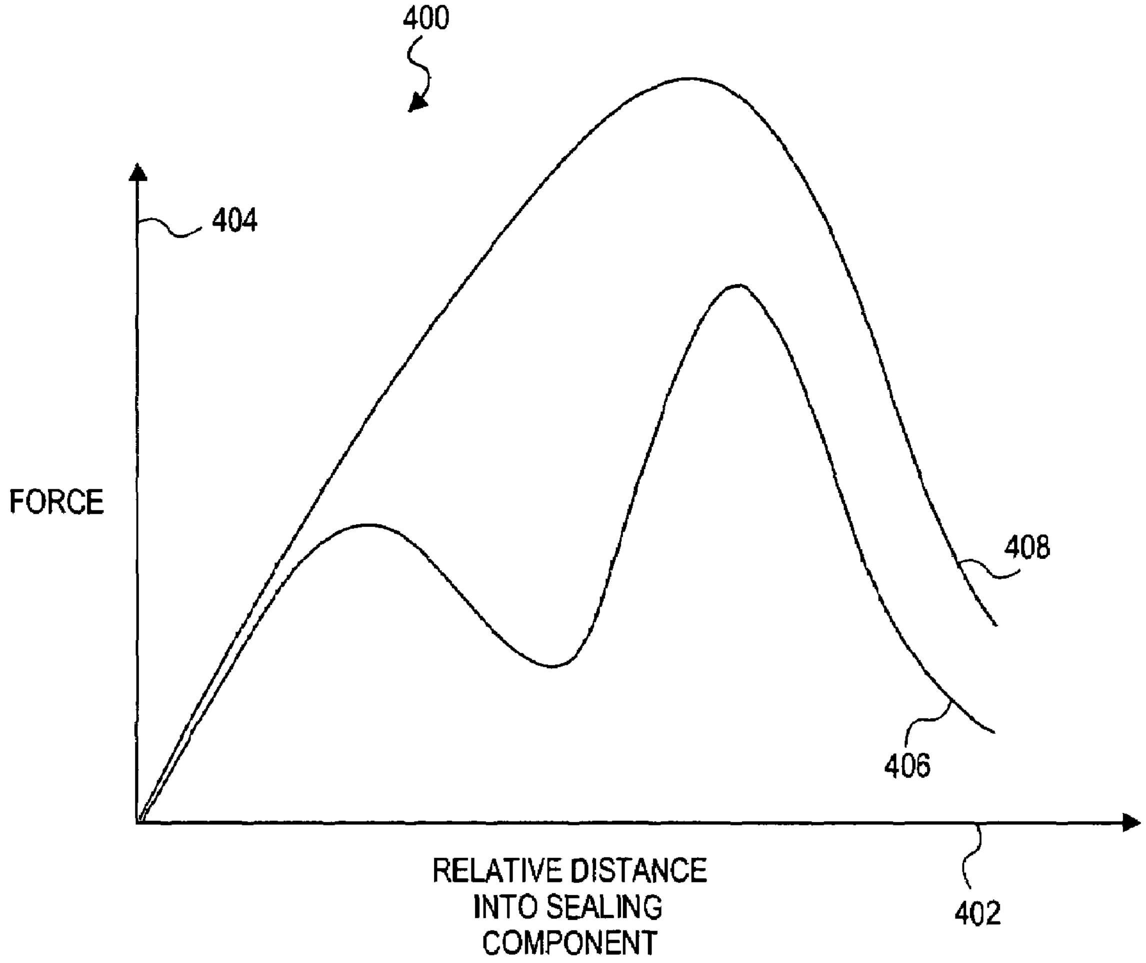
FIG. 4 is a graph illustrating the non-additive insertion force of a mating member being inserted into the sealing component of FIGS. 3A, 3B, 3C, and 3D, according to an exemplary embodiment of the invention.

FIG. 4 shows a graph 400 depicting the relatively low insertion force needed to insert a needle, as the external member, into the exemplary sealing component 106 of FIGS. 3A, 3B, 3C, and 3D, according to an embodiment of the invention. The graph 400 depicts the force needed to insert the needle on the y-axis 404 as a function of the relative distance at which the needle has been inserted into the sealing component 106 on the x-axis 402. The line 406 depicts a force-distance plot when the needle is inserted at the proper end of the sealing component 106, as indicated by the arrow 316, with the assistance of lubricating fluid to push the needle past the region of the interior surface 320 indicated by the arrows 324 and the arrows 322. The line 408, by comparison, depicts a force-distance plot when the needle is inserted at the opposite, wrong end of the sealing component 106, opposite of the arrow 316, such that it encounters the slit 326 first before the region identified by the arrows 324.

The line 406 denotes that the force needed to push the needle first past the region of the interior surface 320 indicated by the arrows 324 is non-additive with the force subsequently needed to push the needle into and through the slit 326. The first hump in the line 406 is the force needed to push the needle past the region of the interior surface 320 indicated by the arrows 324. Once the region has been exceeded, the force needed to further insert the needle into the sealing component 106 drops until the slit 326 is encountered. The second hump in the line 406 is the force needed to push the needle into and through the slit 326. Because the required force drops after needle insertion past the region of the interior surface 320 indicated by the arrows 324, before rising again when the needle encounters the slit 326, it can be considered that the force needed to insert the needle through the region 320 indicated by the arrows 324 is non-additive with the force needed to insert the needle through the slit 326.

By comparison, the line 408 denotes that the force needed to push the needle first into and through the slit 326 is additive with the force subsequently needed to push the needle past or through the region of the interior surface 320 indicated by the arrows 324. That is, once the slit 326 has been encountered by the needle, the force needed to continue pushing the needle through the sealing component 106, past the region of the interior surface 320 identified by the arrows 324, continues to increase. As such, these two forces are additive. Having the forces non-additive, as in the line 406, is advantageous because ultimately less force is required in total to completely push the needle through the sealing component 106, and less force is required at any given time to continue pushing the needle through the sealing component 106.

Figure 5A:
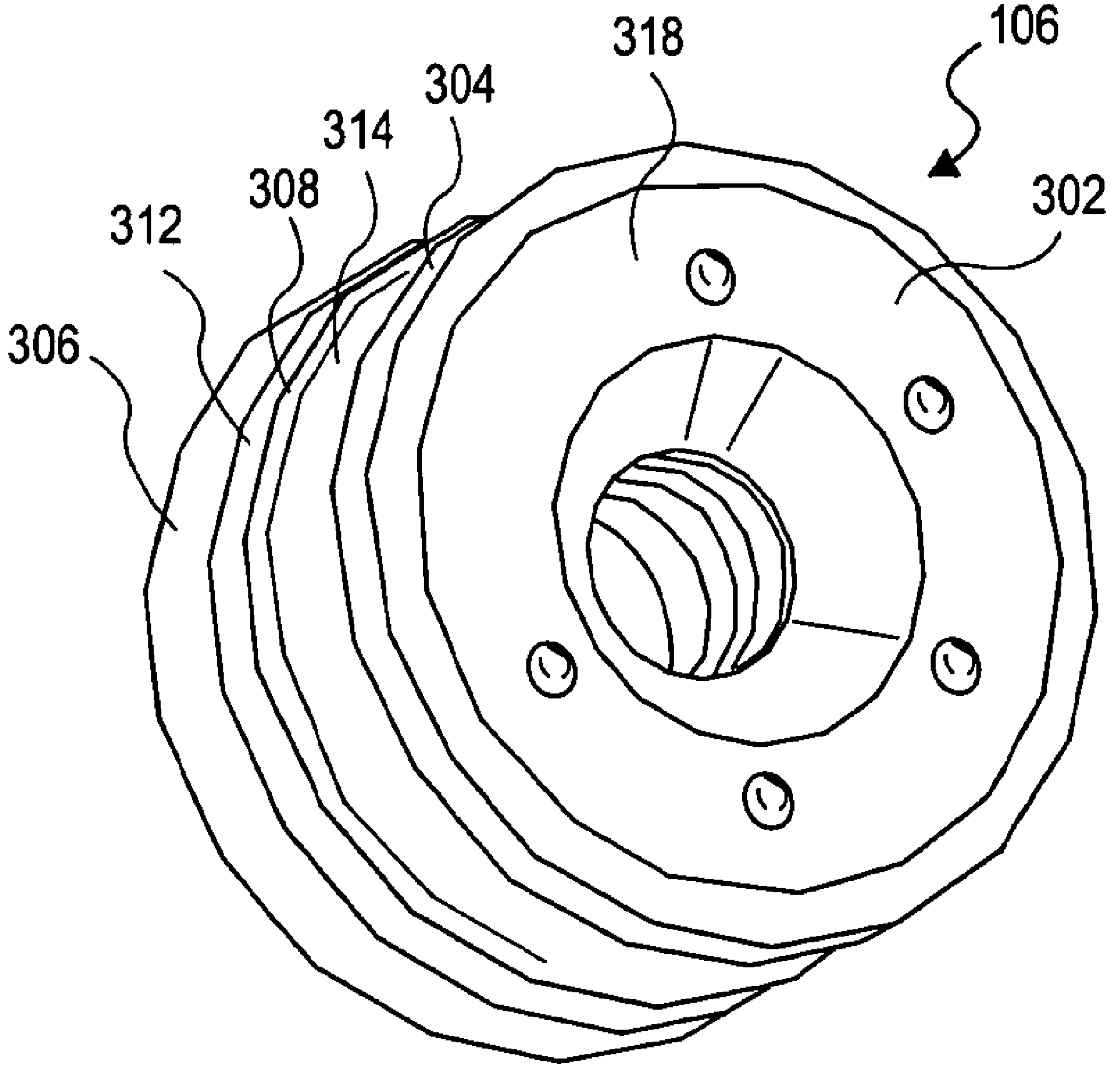
FIGS. 5A, 5B, and 5C are diagrams of a sealing component, according to the same embodiment of the invention of FIGS. 2A, 2B, and 2C.
Figure 5B:
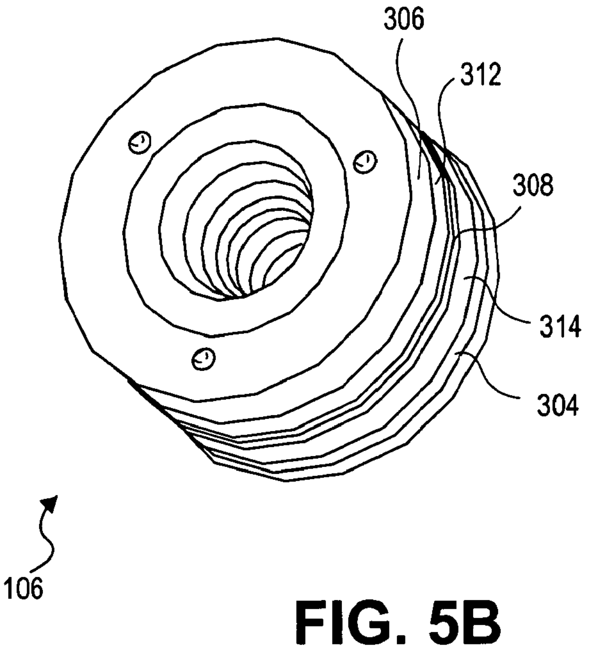
Figure 5C:
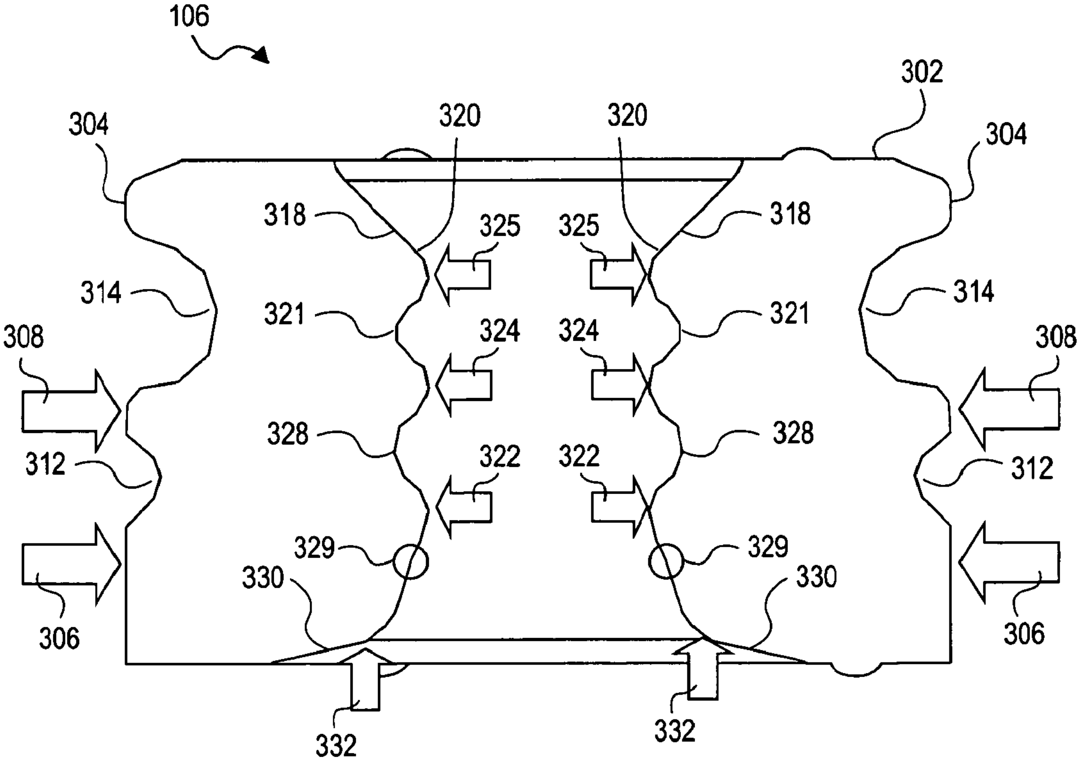

FIGS. 5A, 5B, and 5C show a specific implementation of the sealing component 106, according to another exemplary embodiment of the invention. FIG. 5A shows a top perspective view of the sealing component 106, whereas FIG. 5B shows a bottom perspective view of the sealing component 106. FIG. 5C shows a cross-sectional side view of the sealing component 106. The sealing component 106 is again fabricated from an elastomeric material 302, such as rubber or another elastomeric material. In describing the sealing component 106 of FIGS. 5A, 5B, and 5C, primary reference is made to the cross-sectional side view of FIG. 5C, with supplemental reference as needed to the perspective views of FIGS. 5A and 5B.

The sealing component 106 has an exterior side surface 304. Upon insertion of the sealing component 106 into an external or internal mating member, such as the hole or opening of the enclosure 104 as depicted in FIGS. 1A, 1B, 1C, and 1D, the exterior side surface 304 defines at least one seal with this mating member. That is, the mating member mates with the sealing component 106 to define at least one of the seals indicated by the reference numbers or arrows 306 and 308. Where the hole or opening of the mating member and the sealing component 106 are both round in shape, these seals may be considered annular seals.

When the sealing component 106 is inserted into the mating member, the seals indicated by the reference numbers or arrows 306 and 308 are defined because the elastomeric material 302 at these portions of the exterior side surface 304 are pushed or compressed into a compression region 312. The compression region 312 is a groove notched or otherwise fabricated within, and defined by, the exterior side surface 304 so that the elastomeric material 302 can so compress into the region 312 when these seals are being defined.

The region 314 is a manufacturing tolerance region, the dimensions of which do not affect definition of the seals identified by the reference numbers or arrows 306 and 308. As such, the dimensions of the manufacturing tolerance region can be varied during manufacture or fabrication of the sealing component 106, without affecting the functionality of the seals identified by the reference numbers or arrows 306 and 308.

The exterior side surface 304 of the sealing component 106 is asymmetrically shaped, so that a user is able to easily determine the proper orientation of the sealing component 106 when it is inserted into the mating member. The sealing component 106 of FIGS. 5A, 5B, and 5C is to be inserted into the mating member bottom end first. The region 314 may thus be considered an orientation region defined by the exterior side surface 304 to render the shape of the exterior side surface 304 asymmetric, so that the user is able to easily discern the proper orientation of the sealing component 106.

It is noted that the exterior side surface 304 of the sealing component 106 of FIGS. 5A, 5B, and 5C is oriented upside-down as compared to the exterior side surface 304 of the sealing component 106 of FIGS. 3A, 3B, 3C, and 3D. For instance, the region 314 of the exterior side surface 304 is located towards one end of the sealing component 106 in FIGS. 5A, 5B, and 5C, whereas the region 314 of the exterior side surface 304 is located at the other end of the sealing component 106 in FIGS. 3A, 3B, 3C, and 3D.

Another mating member, such as an external mating member like the needle 110 of the printhead 102 of FIGS. 1A, 1B, 1C, and 1D, is insertable into the sealing component 106. The sealing component 106 has an interior surface 320. The interior surface 320 defines two seals with the mating member, one seal indicated by the arrows 322, and another seal indicated by the arrows 324.

When the mating member is first inserted into the sealing component 106, a lead-in region 318 of the sealing component 106 guides the mating member into the sealing component 106. The lead-in region is thus a downward-ramped region defined by the interior surface 320, which if contacted by the mating member as it is inserted into the sealing component 106, results in the mating member being guided further inward into the sealing component 106. As the mating member passes the region of the interior surface 320 indicated by the arrows 324, the interior surface 320 defines a seal at this region with the mating member. This seal may be considered an annular seal where the interior surface 320 and the mating member each have a round shape.

As the mating member is further inserted into the sealing component 106, it passes the region of the interior surface 320 indicated by the arrows 322. The interior surface 320 defines another seal at this region with the mating member. This seal may also be considered an annular seal where the interior surface 320 and the mating member each have a round shape. Thus, there are two seals defined between the interior surface 320 of the sealing component 106 and the mating member: the seal identified by the arrows 324, and the seal identified by the arrows 322.

Having two seals defined between the interior surface 320 of the sealing component 106 and the mating member inserted into the sealing component 106 provides for redundancy. If one of the seals should fail, the other seal is still present to prevent fluid leakage or escape. Furthermore, the seals indicated by the arrows 322 and 324 are defined because the elastomeric material 302 at these portions of the interior surface 320 are pushed or compressed into a compression region 328. The compression region 328 is a groove or notch removed from or otherwise fabricated within, and defined by, the interior surface 320 so that the elastomeric material 302 can compress into the region 328 when these seals are being defined. In one embodiment, the seals identified by the arrows 322 and 324 are at least substantially identical.

Once the mating member has been inserted into the sealing component 106, it may be removed by being pulled from the sealing component 106. As the mating member is pulled from the sealing component 106, the seal identified by the arrows 322 is first broken. Next, as the member is further pulled from the sealing component 106, the seal identified by the arrows 324 is broken. It is noted that the order of these seals is reversed when the seals are being defined upon insertion of the sealing component 106, where first the seal identified by the arrows 324 is defined by the interior surface 320 with the mating member, and next the seal identified by the arrows 322 is defined by the interior surface 320 with the mating member.

Finally, as the member is further pulled from the sealing component 106, the mating member passes the protrusion of the elastomeric material 302 at the interior surface 320 indicated by the arrows 325. As the member is being pulled from the sealing component 106, any fluid, such as ink, remaining on the sides of the mating member is at least substantially wiped off, or cleaned, by this protrusion. That is, the arrows 325 denote a wiping region defined by the interior surface 320 to at least partially clean the mating member as it is being removed from the sealing component 106.

It is noted that the sealing component 106 of FIGS. 5A, 5B, and 5C does not self-seal when a mating member like a needle is removed from or has not yet been inserted into the sealing component 106. This is in comparison to the sealing component 106 of FIGS. 3A, 3B, 3C, and 3D. The sealing component 106 of FIGS. 3A, 3B, 3C, and 3D features a self-seal capability, where the slit 326 thereof defines a seal with itself when a mating member is removed from or has not yet been inserted into the sealing component 106. Such sealing of the sealing component 106 is desirable to ensure that no fluid escapes or leaks from the sealing component 106 when a mating member is removed from or has not yet been inserted into the sealing component 106.

Therefore, a (third) member, such as an internal mating member like a spring-loaded ball, may be pressed against the exterior bottom surface 330 of the sealing component of FIGS. 5A, 5B, and 5C, as identified by the arrows 332. The exterior bottom surface 330 thus defines a seal with such an internal mating member, like a ball, when the other mating member, like a needle, is being removed from or has not yet been inserted into the sealing component 106 from the component 106. Further discussion of this mating member is made with reference to this member specifically being a ball, whereas further discussion of the mating member inserted into the sealing component 106 is made with reference to the member specifically being a needle, so that the distinction between these two mating members is clear. However, in general, both mating members are still mating members, and are not restricted to a ball and a needle.

Before the needle is inserted into the sealing component 106, the ball and the exterior bottom surface 330 thus define a seal indicated by the arrows 332 so that fluid cannot escape through the sealing component 106. When the needle is inserted into the sealing component 106, it pushes this ball down into the enclosure or supply into which the sealing component 106 has been inserted. Therefore, the needle is able to access the fluid. When the needle is again removed, the ball via its spring-loaded nature pushes or presses against the exterior bottom surface 330 again, to redefine the seal indicated by the arrows 332, so that fluid cannot escape through the sealing component 106.

Two other features of the sealing component 106 of FIGS. 5A, 5B, and 5C are notable. First, there is a slight indentation, or notch or groove, within the interior surface 320 of the sealing component 106, indicated by the reference numbers 329. This indentation serves to separate, or decouple, the functionality of the seal defined by the exterior bottom surface 330 with the ball, as identified by the arrows 332, with the functionality of the seals defined by the interior surface 320 with the needle, as identified by the arrows 322 and 324. Such decoupling means that the seals afforded by elastomeric material 302 relative to the needle are not affected by the seals afforded by the elastomeric material 302 relative to the ball.

For instance, when the needle is being inserted into the sealing component 106, the presence of the slight indentation at least substantially reduces, if not totally eliminating, distortion or compression of the elastomeric material 302 that may otherwise affect the seal with the ball. That is, the potential for the elastomeric material 302 to distort and affect the seal with the ball is reduced. Resultingly, the potential for leakage to occur at the seal with the ball during needle insertion is reduced due to the presence of the indentation identified by the reference numbers 329. It is noted that such undesirable distortion or compression of the elastomeric material 302 is further reduced or eliminated as a result of there being two seals with the needle, due to the compression region 328 being present between these two seals.

Second, there is a notch or groove 321 that separates the top of the sealing component 106 from the seals with the needle identified by the arrows 322 and 324. This notch 321 helps to define the wiping region identified by the arrows 325 within the interior surface 320. Furthermore, the notch 321 isolates the seals identified by the arrows 322 and 324 from the top of the sealing component 106. Any irregular pressure on the top of the sealing component 106, such as resulting from a user pushing on the top of the sealing component 106, is thus less likely to affect the ability of the elastomeric material 302 to define and maintain the seals identified by the arrows 322 and 324.

Figure 6:
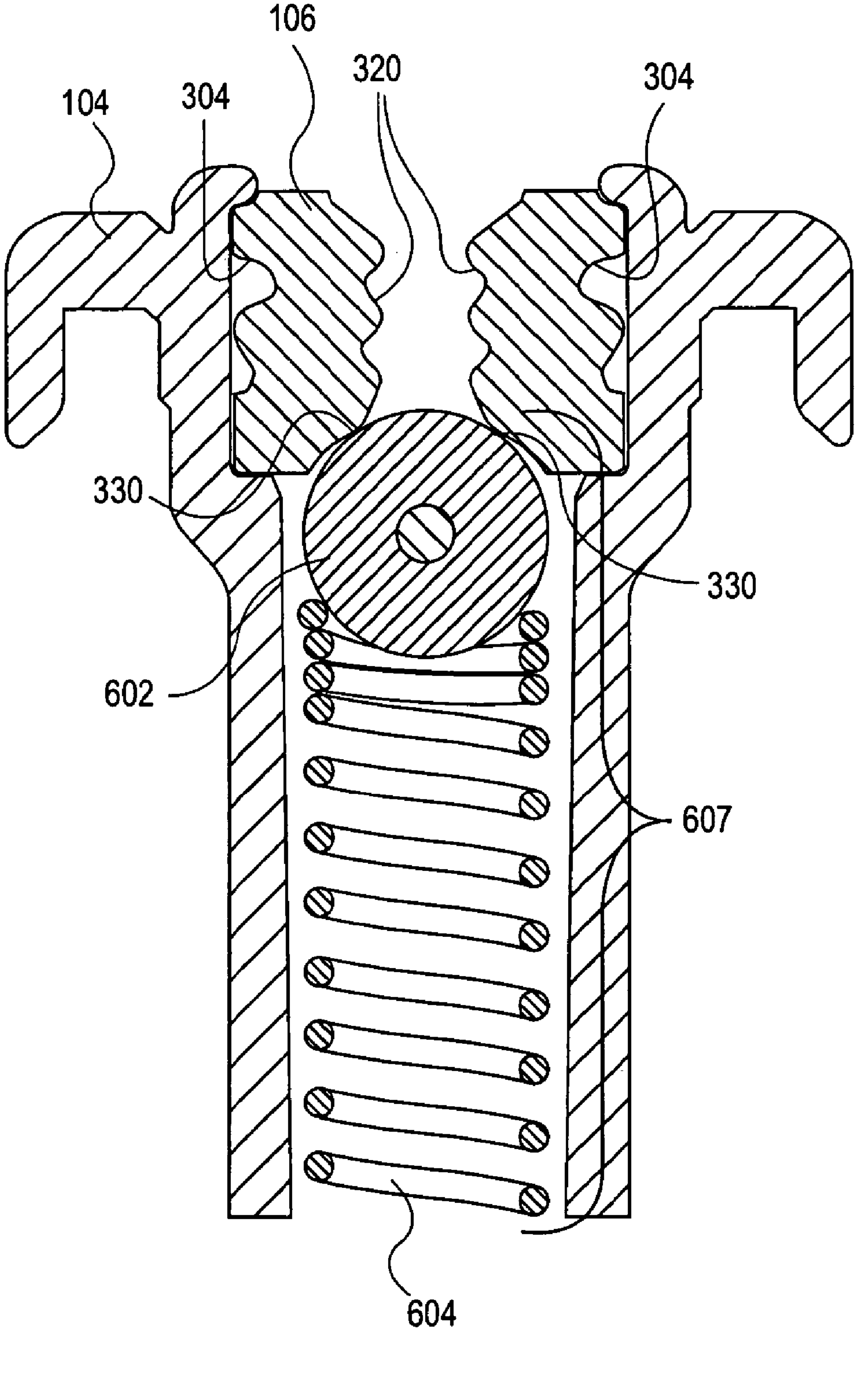
FIG. 6 is a diagram of a mating member pressing against a bottom surface of the sealing component of FIGS. 5A, 5B, and 5C when another mating member is not inserted into the sealing component, according to an exemplary embodiment of the invention.

FIG. 6 shows a specific implementation of an internal mating member 601 pressing against the exterior bottom surface 330 of the sealing component 106, according to an exemplary embodiment of the invention. The mating member 601 includes a ball 602, as has been described, and a spring 604. The ball 602 is spring-loaded by virtue of coupling with the spring 604. As depicted in FIG. 6, the sealing component 106 has been inserted into the enclosure 104, such that its exterior side surface 304 defines seals with the enclosure 104 so that fluid cannot escape around the sealing component 106 along the exterior side surface 304.

When a mating member such as a needle has been removed from or has not yet been inserted into the sealing component 106, the ball 602 presses against the exterior bottom surface 330 of the sealing component 106, due to the force exerted by the spring 604. The exterior bottom surface 330 thus defines a seal with the mating member 601, specifically the ball 602 thereof, so that fluid cannot escape or leak through the sealing component 106 along the interior surface 320. When the needle or other mating member is inserted into the sealing component 106, it pushes down against the ball 602. The seal defined by the exterior bottom surface 330 with the mating member 601 is thus broken, and the needle or other mating member can access the fluid. That is, the needle pushes the ball 602 away so that it can access the fluid. Fluid cannot escape or leak along the interior surface 320 around this needle or other mating member, due to the seals defined by the interior surface 320 with the needle, as have been described.

As the needle or other mating member is removed from the sealing component 106, the spring 604 pushes the ball 602 towards or against the exterior bottom surface 330, so that a seal is again defined by the exterior bottom surface with the mating member 604. Thus, at no time can fluid leak or escape through the sealing component 106 along its interior surface 320. At any given time, either the interior surface 320 is defining one or more seals with the needle, or the exterior bottom surface 330 is defining a seal with the mating member 601.

Figure 7:
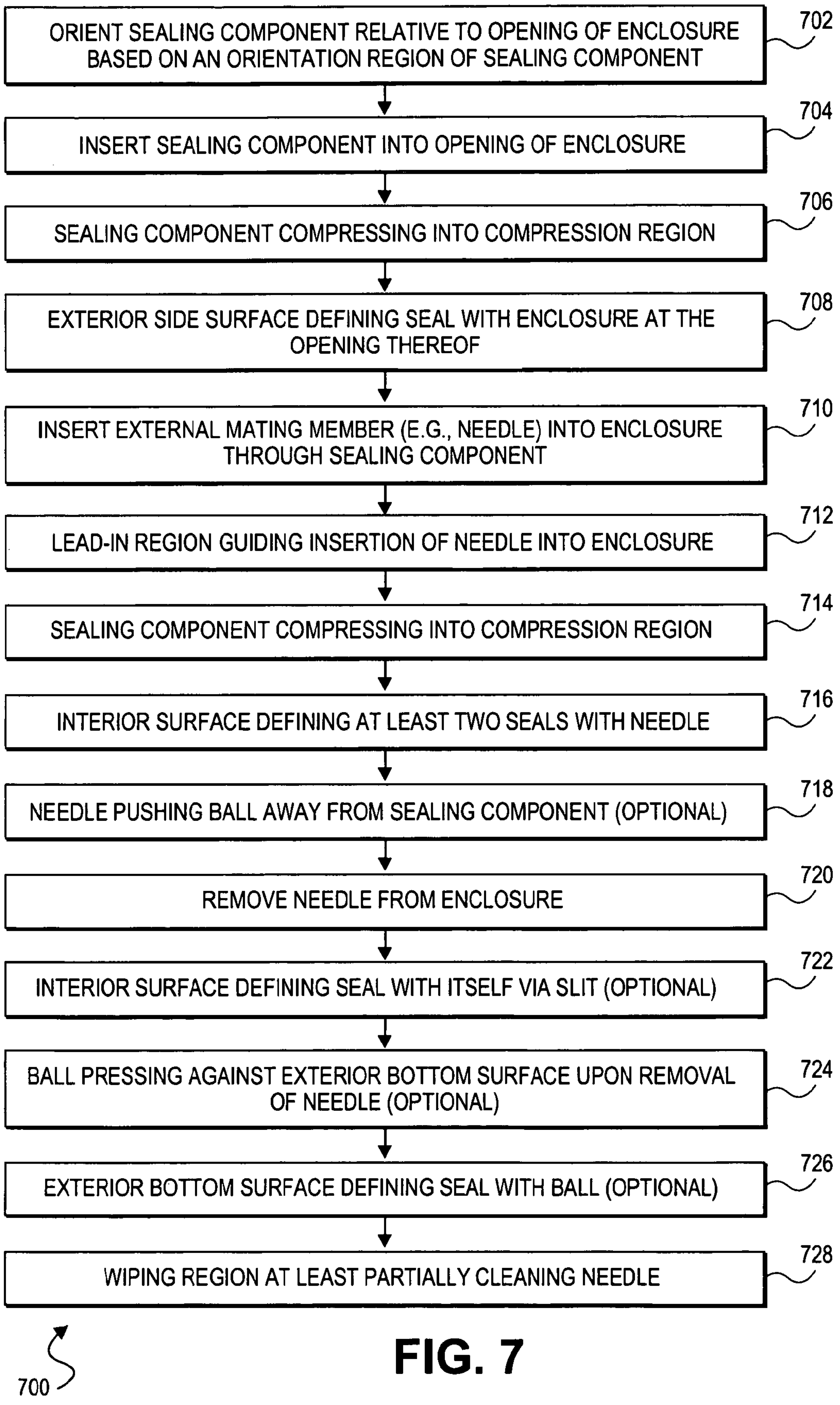
FIG. 7 is a flowchart of a method of use, according to an exemplary embodiment of the invention.

FIG. 7 shows a method 700, according to an embodiment of the invention. The method 700 may be performed relative to the sealing component of FIGS. 3A, 3B, 3C, and 3D that has been described, or it may be performed relative to the sealing component of FIGS. 5A, 5B, and 5C that has been described. The sealing component is first oriented by a user relative to an opening of an enclosure, based on an orientation region of the sealing component (702). The sealing component can then be inserted into the opening of the enclosure since it is now properly oriented and thus inserted right side up (704). Insertion of the sealing component into the enclosure causes elastomeric material of the sealing component to compress into a compression region of an exterior side surface of the sealing component (706), resulting in the exterior side surface defining at least one seal with the enclosure at the opening of the enclosure (708). Not shown in FIG. 7 is that the enclosure may be filled with fluid, such as ink, either before or after the sealing component has been inserted into the enclosure, although typically the enclosure is filled with fluid after the sealing component has been inserted into the enclosure.

Next, an external mating member, such as a needle, is inserted into the enclosure through the sealing component (710). A lead-in region of the sealing component may guide insertion of the needle into the enclosure (712). Insertion of the needle into the sealing component causes elastomeric material of the sealing component to compress into a compression region of an interior surface of the sealing component (714). As a result, the interior surface defines at least two seals with the needle in succession, as the needle is inserted into the sealing component (716). Furthermore, in one embodiment, where the sealing component is that of FIGS. 5A, 5B, and 5C, insertion of the needle into the sealing component causes the needle to push away a ball from the exterior bottom surface of the sealing component (718).

At some point, the needle is removed from the enclosure (720). For instance, the needle may have been used to fill the enclosure with fluid, or the needle may have been used to extract fluid from the enclosure, such that either such process is finished, and the needle removed. In one embodiment, where the sealing component is that of FIGS. 3A, 3B, 3C, and 3D, removal of the needle results in the interior surface of the sealing component defining a seal with itself via a slit (722). In another embodiment, where the sealing component is that of FIGS. 5A, 5B, and 5C, removal of the needle results in the ball pressing against the bottom exterior surface of the sealing component (724), such that the bottom exterior surface defines a seal with the ball (726). Finally, a wiping region of the sealing component at least partially cleans the needle as the needle is removed from the enclosure through the sealing component (728).

It is noted that, although specific embodiments have been illustrated and described herein, it will be appreciated by those of ordinary skill in the art that any arrangement calculated to achieve the same purpose may be substituted for the specific embodiments shown. For example, whereas some embodiments of the invention have been described in relation to a sealing component for an ink supply that then mates with an inkjet printhead or an inkjet printhead component, other embodiments of the invention can be employed in relation to applications other than inkjet-printing devices. This application is thus intended to cover any adaptations or variations of the disclosed embodiments of the present invention. Therefore, it is manifestly intended that this invention be limited only by the claims and equivalents thereof.

We claim:

1. A method comprising:

inserting a sealing component into an opening of an enclosure;

an exterior side surface of the sealing component defining at least a first exterior seal with the enclosure at the opening thereof;

inserting an external mating member into the enclosure through the sealing component; and, an interior surface of the sealing component defining first and second interior seals with the external mating member upon insertion of the external mating member into the enclosure through the sealing component, including defining the first interior seal with the external mating member prior to defining the second interior seal with the external mating member, wherein the interior surface of the sealing component is substantially curved in a region of the first interior seal prior to the first interior seal being defined with the external mating member, and remains substantially curved in the region of the first interior seal upon the first interior seal being defined with the external mating member.

2. The method of claim 1, further comprising compressing the sealing component into a compression region of the exterior side surface of the sealing component upon insertion of the sealing component into the opening of the enclosure.

3. The method of claim 1, further comprising orienting the sealing component relative to the opening of the enclosure based on an orientation region of the exterior side surface of the sealing component so that the sealing component is properly oriented within the opening of the enclosure.

4. The method of claim 1, further comprising guiding insertion of the external mating member into the enclosure through the sealing component via a lead-in region of the interior surface of the sealing component.

5. The method of claim 1, further comprising:

removing the external mating member from the enclosure through the sealing component, such that the second internal seal is first broken and the first internal seal is next broken as the external mating member is removed; and, a wiping region of the interior surface of the sealing component at least partially cleaning the external mating member as the external mating member is removed.

6. The method of claim 1, further comprising compressing the sealing component into a compression region of the interior surface upon insertion of the external mating member into the enclosure through the sealing component.

7. The method of claim 1, further comprising:

the external mating member pushing another mating member away from the sealing component upon insertion of the external mating member into the enclosure through the sealing component;

the other mating member pressing against a bottom surface of the sealing component upon removal of the external mating member from the enclosure through the sealing component; and, the bottom surface of the sealing component defining a bottom seal with the other mating member.

8. The method of claim 1, wherein the interior surface of the sealing component defines the second interior seal with the external mating member via the external mating member being pushed through a slit within the interior surface of the sealing component.

9. The method of claim 1, further comprising the interior surface of the sealing component defining an interior seal with itself via a slit that closes upon the removal of the external mating member from the enclosure through the sealing component.

10. The method of claim 1, further comprising the exterior side surface of the sealing component further defining a second exterior seal with the enclosure at the opening thereof.

11. The method of claim 1, wherein defining the first interior seal with the external mating member prior to defining the second interior seal with the external mating member includes the external mating member contacting the first interior seal before contacting the second interior seal.

12. The method of claim 1, wherein a sealing surface of the first interior seal is collinear with a sealing surface of the second interior seal upon insertion of the external mating member into the enclosure through the sealing component.

* * * * *